United States Patent [19]

Frey

[11] 4,031,570
[45] June 28, 1977

[54] PROSTHETIC ACETABULUM

[75] Inventor: Otto Frey, Winterthur, Switzerland

[73] Assignee: Sulzer Brothers Limited, Winterthur, Switzerland

[22] Filed: May 27, 1976

[21] Appl. No.: 690,717

[30] Foreign Application Priority Data
June 18, 1975 Switzerland .................... 7898/75

[52] U.S. Cl. .............................. 3/1.912; 128/92 C
[51] Int. Cl.² ......................................... A61F 1/24
[58] Field of Search .............. 3/1.912, 1.913, 1.91, 3/1; 128/92 C, 92 CA

[56] References Cited
UNITED STATES PATENTS

| 3,521,302 | 7/1970 | Muller | 3/1.91 |
| 3,658,056 | 4/1972 | Huggler et al. | 3/1.91 X |

FOREIGN PATENTS OR APPLICATIONS

| 2,229,812 | 1/1974 | Germany | 3/1.912 |

Primary Examiner—Ronald L. Frinks
Attorney, Agent, or Firm—Kenyon & Kenyon, Reilly, Carr & Chapin

[57] ABSTRACT

The concave articular surface of the prosthetic acetabulum which receives a spherical joint head is formed with a groove which extends about the surface and joint head. This groove serves to distribute the lubricant within the joint during loading and unloading of the joint.

3 Claims, 1 Drawing Figure

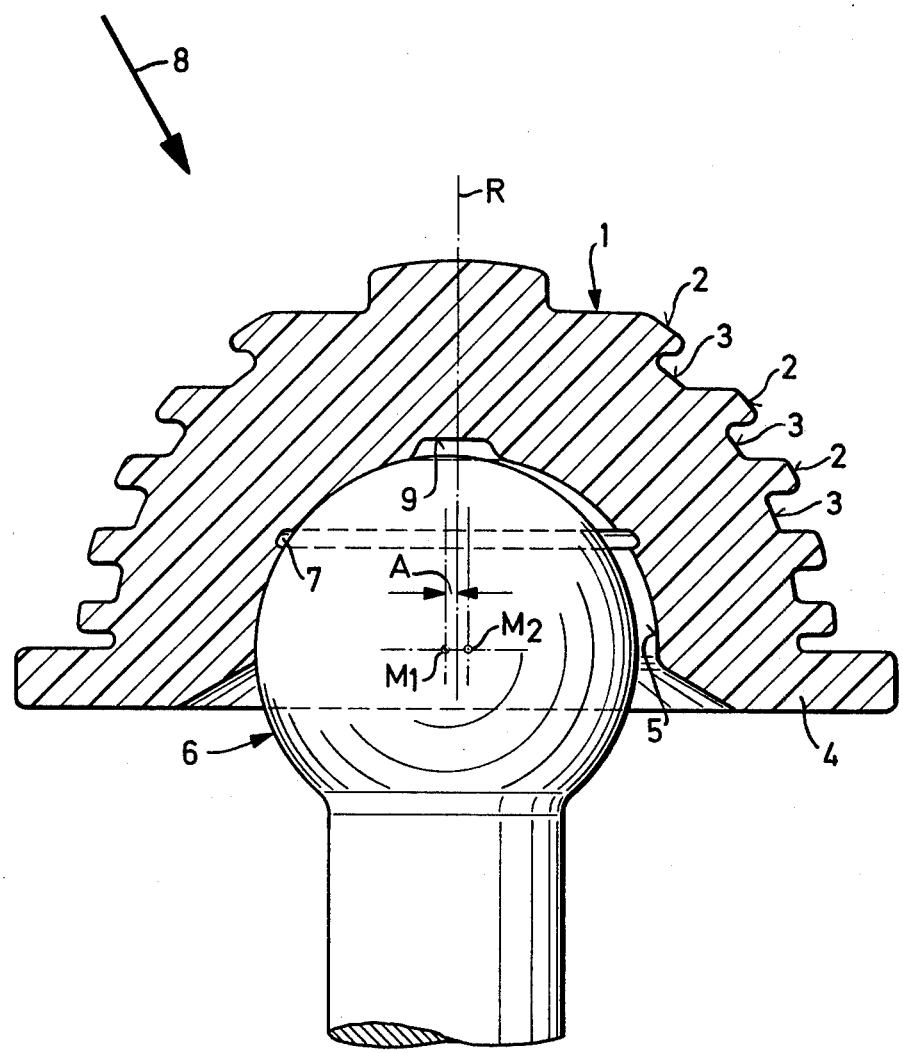

PROSTHETIC ACETABULUM

This invention relates to a prosthetic acetabulum, and particularly, to a prosthetic acetabulum of a total endoprosthesis for a hip joint.

As is known, there are many types of total endoprostheses available for use in hip joint repair or replacement. Generally, these total endoprostheses employ a prosthetic acetabulum with a concave spherical surface and a hip joint prosthesis with a spherical joint head which fits into the acetabulum. While many of these endoprostheses are suitable for a period of time, they usually suffer from a common problem. That is, these prostheses are subject to a considerable amount of wear. Consequently, after some time, it becomes necessary to replace these endoprostheses or to somehow make adjustments. In either case, the patient is subject to discomfort at the least.

Heretofore, the problem of wear of the rubbing surfaces of endoprosthetic joints has not been solved satisfactorily. Consequently, endeavors have been made, particularly for the case in which the spherical joint head rubs in conditions of heavy loading in an acetabulum of a total hip joint prosthesis, to achieve synovial lubrication between the rubbing surfaces. However, such endeavors have very often been unsatisfactory because of the high surface pressures and of the narrow gaps left between the rubbing surfaces.

Accordingly, it is an object of the invention to improve the synovial lubrication of an endoprosthesis for a hip joint.

It is another object of the invention to improve the lubrication of a hip joint prosthesis in a relatively simple manner.

Briefly, the invention provides a prosthetic acetabulum for a hip joint endoprosthesis which has a concave articular surface for receiving a spherical joint head and at least one recessed groove within the surface which extends peripherally of the surface. This groove serves to distribute lubricant, particularly synovial liquid, about the prosthesis during loading and unloading. The effect is particularly obtained when the acetabulum diameter is slightly greater than joint head diameter since the liquid which is displaced when the joint is loaded on one side of the acetabulum collects in the groove. Thus, when the pressure between the pressed-together surfaces ceases, the collected liquid wets such surfaces satisfactorily with the formation of an adequate lubricating film. In addition, liquid is also displaced from the volume which is present on the unloaded side of the joint, which volume diminishes as the load decreases, through the groove between the previously pressed-together rubbing surfaces.

The acetabulum is particularly useful in combination with a hip joint prosthesis having a joint head with a spherical surface.

The groove can be of any kind, e.g. an annular groove or a helical groove, provided that the free ends of the groove are disposed within the hollow spherical articular surface which the joint head seals when the joint is under load.

In order to improve the lubricating effect, the concave articular surface of the acetabulum is made as a surface of rotation whose generatrix is a quadrant arc with a radius corresponding to the radius of the spherical surface of the joint head but having a center of curvature of the generatrix spaced a predetermined distance from the rotational axis of the surface of rotation of the acetabulum. In this event, the distance can be, conveniently, from 0.1 to 0.5 millimeters mm. To further improve lubrication, the articular surface has a pocket near the apex of the surface.

These and other objects and advantages of the invention will become more apparent from the following detailed description and appended claims taken in conjunction with the accompanying drawing in which:

The FIG. illustrates a sectional view of an acetabulum according to the invention in which an associated joint head is shown as experiencing an assumed load acting in the direction of the arrow in the top left-hand part of the FIG.

Referring to the drawing, an acetabulum 1, shown to an enlarged scale and made, with advantage, of high-molecular hard polyethylene, is formed on a concave exterior with annular projections 2 and recesses 3 for improved anchorage in a hip bone. Preferably, the anchorage is produced by means of a known methylmethacrylate-based bone cement. At the equator, the hemispherical acetabulum 1 terminates in a flange 4 which merges by way of bevelling into a concave internal articular surface 5.

The concave surface 5 is adapted to receive a spherical joint head 6 of a hip joint prosthesis which is not shown in greater detail and which is adapted to be anchored in a thigh bone. Preferably, the hip joint prosthesis is made of one of the metals used in the implant art or of a metal alloy, although the head can be made of a bioceramic, e.g. very pure aluminum oxide ($Al_2O_3$). In the drawing, the position of the acetabulum 1 relative to the head 6 is shown as it arises when a load acting in the direction of arrow 8 acts on the joint.

The concave acetabulum surface 5 is formed with an annular groove 7 which extends about the surface 5 and the joint head 6. In addition, according to another feature of the invention, the concave acetabulum surface 5 is not a hollow spherical surface but a surface of rotation arising by rotation of a quadrant arc around the longitudinal axis R of the acetabulum 1, the arc having the same radius as the associated joint head 6 but the arc center M being offset from the axis R by a small amount A of e.g. approximately from 0.1 to 0.5 millimeters (mm). Consequently, the joint head 6 has an increased clearance in the acetabulum 1 when loads are applied and cease to be applied. However, there is no reduction in the bearing component surfaces which, when the head 6 and the acetabulum 1 are of the same diameter, are relatively large, i.e. relative to the bearing component surfaces of the known acetabula whose diameter is larger than the diameter of the heads. Of course, a groove 7 according to the invention can be used in known acetabula which are of hollow spherical shape and whose diameter is greater than the diameter of the joint head 6.

A pocket 9 is also formed at the apex of the concave acetabulum surface 5 so that when the joint is loaded, further liquid can be displaced into and stored in the pocket 9. When joint loading decreases, the liquid thus stored in the pocket 9 can discharge therefrom as an extra lubricating film on the rubbing surfaces.

The articular acetabulum surface 5 can be produced e.g. by chip-removing machining of the rotating acetabulum 1 by means of a tool moving along a corresponding curve or by means of a tool which moves on a circular arc and which is offset from the axis of rotation of the acetabulum 1.

As already briefly indicated, the groove 7 serves as a collector for synovia which is displaced when the joint is loaded, the synovia returning between the rubbing surfaces when the load decreases. Also, the fact that communication exists with a volume on the previously loaded side of the joint, such volume diminishing as the load decreases, enables liquid to flow through the groove 7 into the region between the surfaces which rub on one another when the joint is loaded.

As also noted above, the groove 7 may be a helical groove or any other peripheral groove wherein the terminal ends are disposed within the hollow spherical articular surfaces which the joint head 6 seals when the joint is under load.

It is noted that the acetabulum surface 5 and the spherical joint head 6 have the same radius of curvature. Because of this, the bearing pattern of the support of the spherical head 6 in the acetabulum 1 is improved. That is, the bearing surface between the spherical head 6 and the acetabulum 1 is larger than those prostheses in which the acetabulum has a slightly larger radius than the spherical head. As a result, the loads are distributed over a larger surface and pressure peaks are avoided. In the case of plastic acetabulums, the risk of cold flow of the plastic under high pressures is reduced. Further, with the usual measurements of hip joint sockets, it is much easier to satisfy the imperical rule that there should be at least one centimeter of support surface for every 100 kg (killograms) of load.

The clearance provided between the spherical head 6 and the acetabulum 1 allows a lubricating agent to flow into the socket, particularly from the pocket 9 and groove 7, without the contact surface between the head 6 and acetabulum 1 becoming smaller.

What is claimed is:

1. A hip joint endoprosthesis comprising
a joint head with a spherical surface; and
a prosthetic acetabulum having a concave articular surface receiving said joint head and at least one groove within said surface extending peripherally of said surface and said joint head, said articular surface being a surface of rotation having as a generatrix a quadrant arc with a radius corresponding to the radius of said joint head spherical surface but a center of curvature spaced a predetermined distance from the rotational axis around which said quadrant arc is rotated for generating said surface of rotation of said acetabulum.

2. A hip joint endoprosthesis as set forth in claim 1 wherein said distance is from 0.1 millimeters to 0.5 millimeters.

3. A hip joint endoprosthesis as set forth in claim 1 wherein said concave surface has a diameter greater than the diameter of said spherical joint head.

* * * * *